(12) United States Patent (10) Patent No.: US 7,566,421 B2
Fike (45) Date of Patent: Jul. 28, 2009

(54) ENCAPSULATED SORBENT TUBE

(75) Inventor: Randall Stuart Fike, Clarkston, MI (US)

(73) Assignee: Prism Analytical Technologies, Inc., Mt. Pleasant, MI (US)

( * ) Notice: Subject to any disclaimer, the term of this patent is extended or adjusted under 35 U.S.C. 154(b) by 318 days.

(21) Appl. No.: 10/176,938

(22) Filed: Jun. 21, 2002

(65) Prior Publication Data

US 2003/0235515 A1    Dec. 25, 2003

(51) Int. Cl.
G01N 30/96 (2006.01)
G01N 21/00 (2006.01)
G01N 1/22 (2006.01)
G01J 1/48 (2006.01)

(52) U.S. Cl. ............... 422/69; 422/60; 422/59; 422/86; 422/57; 436/181

(58) Field of Classification Search ........ 422/68.1, 422/83, 99, 101, 102, 104, 312, 913, 88, 422/69, 60, 59, 86, 57; 436/181
See application file for complete search history.

(56) References Cited

U.S. PATENT DOCUMENTS

| | | | | |
|---|---|---|---|---|
| 1,924,914 A | * | 8/1933 | Comstock | 62/85 |
| 2,371,405 A | * | 3/1945 | Munn | 422/59 |
| 3,022,141 A | * | 2/1962 | Grosskopf | 422/60 |
| 3,676,073 A | * | 7/1972 | Luckey | 436/178 |
| 4,003,257 A | * | 1/1977 | Fletcher et al. | 73/19.02 |
| 4,071,319 A | * | 1/1978 | Nugent | 422/59 |
| 4,272,479 A | * | 6/1981 | Huneke et al. | 422/57 |
| 4,315,890 A | * | 2/1982 | Tamers | 422/58 |
| 4,425,438 A | * | 1/1984 | Bauman et al. | 436/527 |
| 4,460,544 A | * | 7/1984 | Leichnitz | 422/59 |
| 4,481,297 A | * | 11/1984 | Zucal et al. | 436/181 |
| 4,643,032 A | | 2/1987 | Lawrenz et al. | |
| 4,769,218 A | * | 9/1988 | Leichnitz et al. | 422/86 |
| 5,180,554 A | * | 1/1993 | Yamaguchi et al. | 422/86 |
| 5,328,664 A | * | 7/1994 | Ponsy | 422/84 |
| 5,482,677 A | * | 1/1996 | Yao et al. | 422/88 |
| 6,048,495 A | * | 4/2000 | Marcoll | 422/60 |
| 6,125,709 A | * | 10/2000 | Van Der Maas | 73/863.23 |
| 6,244,117 B1 | | 6/2001 | Mengel et al. | |
| 7,077,017 B2 | * | 7/2006 | Beaton | 73/863.23 |
| 7,318,910 B2 | * | 1/2008 | Kin et al. | 422/88 |

* cited by examiner

*Primary Examiner*—Jill Warden
*Assistant Examiner*—Lore Jarrett
(74) *Attorney, Agent, or Firm*—James P. Hanrath

(57) ABSTRACT

An encapsulated sorbent tube includes a sampling sorbent tube having an open end and containing a sorbent material therein enclosed within an independent encapsulation element that has a body portion and an end portion. The body portion of the encapsulation element has an inner diameter greater than the outer diameter of the sampling sorbent tube sufficient to accommodate the sampling sorbent tube therein. The end portion of the encapsulation element is formed and defined by the longitudinal length of the encapsulation element in excess of the sampling sorbent tube, and includes a proximal frangible element and a distal closure seal, each being independent of and separated from the sampling sorbent tube.

7 Claims, 2 Drawing Sheets

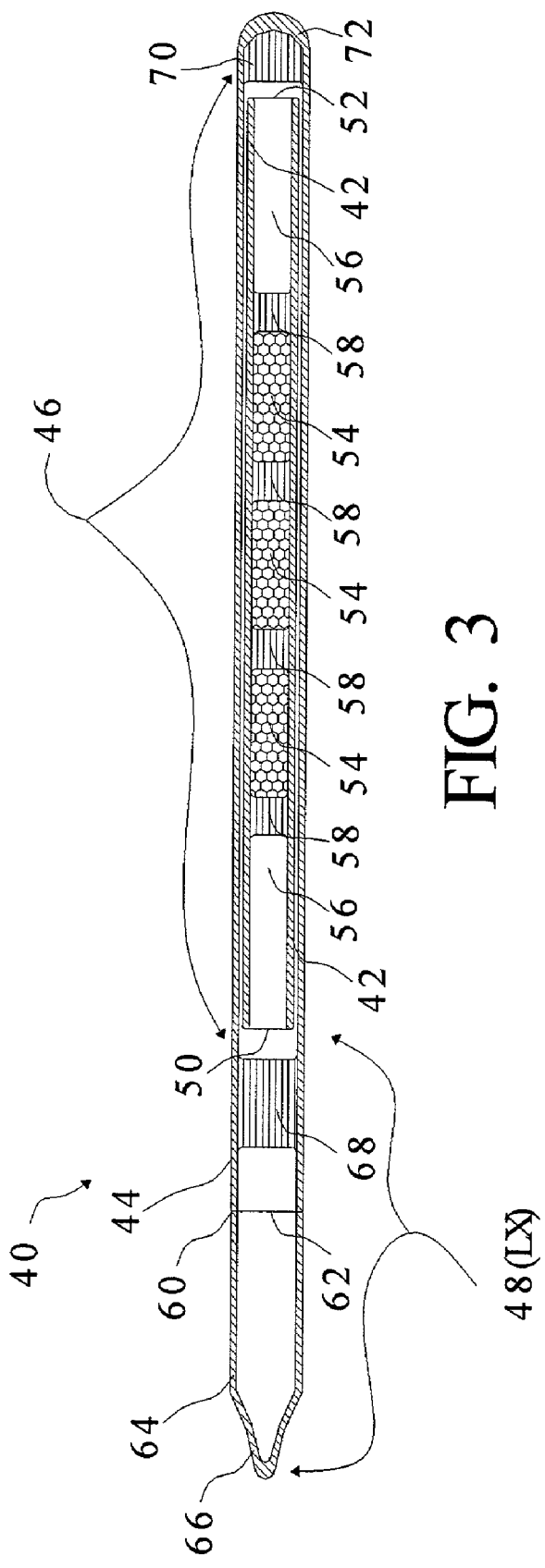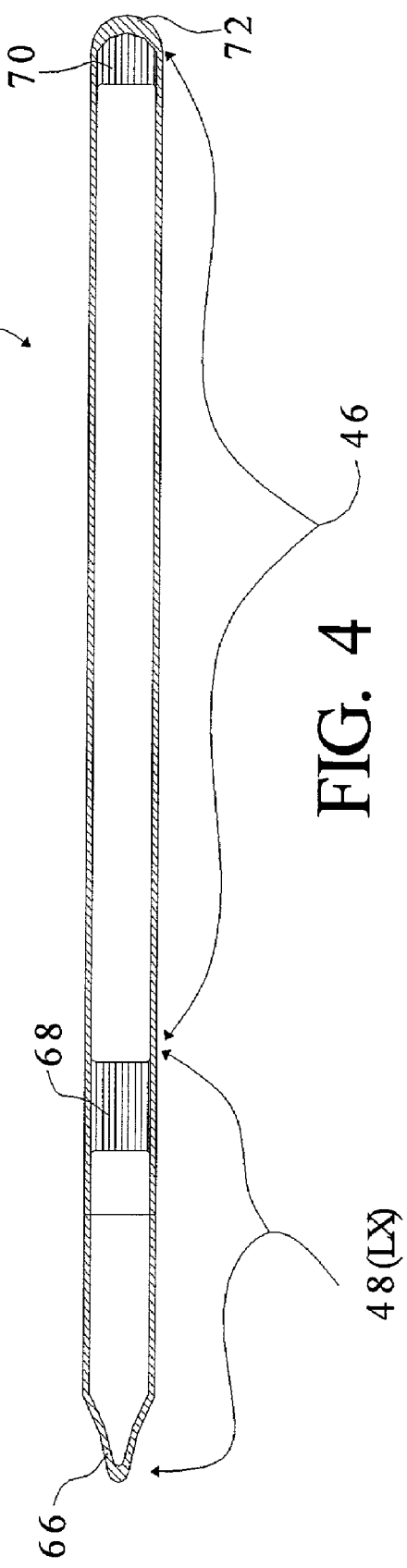

ENCAPSULATED SORBENT TUBE

BACKGROUND OF THE INVENTION

1. Field of the Invention

The present invention relates generally to sorbent tube sampling devices for determining the nature and quantity of chemical and biological contaminants in air and other gases, and particularly to a encapsulated sorbent tube which has a frangible encapsulation element and which is independent of and protective of a sampling sorbent tube contained therein.

2. Description of the Related Art Including Information Disclosed Under 37 CFR 1.97-1.99

There is a large and continuing need for identifying and monitoring the level of pollutants or contaminants in air and in industrial gas streams. This need is often addressed by obtaining a sample of the air at the monitoring site and transporting the sample to a laboratory for analysis. Samples may be obtained by manually filling a sampling container such as a plastic bag, a hypodermic syringe, or an evacuated metal or glass vessel, and sealing it for transportation. However, sampling devices that take a bulk air sample for transport and later analysis are often inappropriate for use in circumstances in which the contaminant being monitored is present in small concentrations, in the parts per billion or even parts per trillion range. The size of the sample that is collected is often too small for the contaminant to be detected and its concentration measured. That requirement has led to the development of sampling devices that preferentially extract and trap the contaminants from the sampled air or gas stream and hold the trapped contaminant for later release and analysis. Sampling sorbent tubes are among such devices as the tube contains a sorbent material that functions to extract and hold contaminants from an air stream passing through the tube. Because most contaminants of interest are organic compounds, the sorbent material is chosen to absorb those compounds while allowing air and inorganic compounds to pass through the tube substantially unimpeded. There exist a variety of thermal desorption or sampling sorbent tubes which are used to extract and retain volatile organic compounds from air flowing through them during the sampling period for later analytical determination of the volatile organic compounds contained in the air. When such sampling sorbent tubes are loaded onto an analytical instrument, the retained volatile organic compounds are liberated using thermal desorption and allowed to flow into the analytical instrumentation. Analysis of the liberated volatile organic compounds is then accomplished using any of several analytical instruments or using a combination thereof.

The foregoing sampling sorbent tubes require that the tube be maintained in a contaminant-free condition prior to air sampling at the monitoring site. In this regard, the sampling sorbent tube may be manufactured to have a body portion internally containing desired sorbent material and lateral end portions that are either capped with plastic over-caps or screw threaded end caps. Alternatively, the sampling sorbent tube itself may be formed to be of an integral closed construction having its lateral ends enclosed for a later breakage by a user at a monitoring site to then expose the central body portion containing the desired sorbent material.

In the former case of capped sampling sorbent tubes, the capping of open sorbent tube ends may not form a perfect, airtight seal and, therefore, may permit the exchange of surrounding air with the air inside the sampling sorbent tube. Any volatile organic compounds contained in the air passing into the thermal desorption tube during storage and/or transport to a monitoring site are adsorbed onto the sorbent contained therein and are, during the subsequent analysis, desorbed into the analytical instrument and are manifest as interferences, background, or sample overlap. Because of these deleterious analytical interferences or the potential thereof, the amount of time that capped sorbent sampling tube can be stored prior to actual monitoring site use is greatly reduced. In addition, the user is afforded no assurance that the thermal desorption tube has been stored in a clean environment and is free of contamination.

In the latter case of the sampling sorbent tube itself being formed with integral closed ends for later breakage to expose a central body portion of the tube at a monitoring site, such sampling sorbent tubes are designed to be disposable being suited for one time usage due to the structural integrity of the tube itself being damaged by breakage of their ends to achieve exposure of the central body portion of the tube. Since the sampling sorbent tube must be broken near its sealed ends, it necessarily is of a thin walled construction to permit such breakage. However, such a construction may make the sampling sorbent tube itself more prone to mechanical damage during shipping and handling. Still further, as the sampling sorbent tube itself is damaged during breakage of its sealed ends, a user may be exposed to glass shards at a breakage site which may injure the user. In addition, the break may produce crack initiation lines that may propagate into the useable body portion of the sampling sorbent tube compromising its integrity thereby diminishing or threatening its usefullness.

SUMMARY OF THE INVENTION

According to the present invention, there is provided an encapsulated sorbent tube comprising a sampling sorbent tube having an open end and containing a sorbent material therein, an encapsulation element independent of the sorbent sampling tube having a body portion and an end portion, the body portion of the encapsulation element having an inner diameter greater than the outer diameter of the sampling sorbent tube sufficient to accommodate the sampling sorbent tube therein, the encapsulation element having a longitudinal length in excess of the sampling sorbent tube, such excess length forming the end portion of the encapsulation element, and the end portion of the encapsulation element having a proximal frangible element and a distal closure seal, each being independent of and separated from the sampling sorbent tube.

The present invention advantageously provides for a sampling sorbent tube independent of, isolated from, and protected by its frangible encapsulation element enclosure. As the sampling sorbent tube itself is not part of the distal closure seal of the encapsulation element, it is not damaged when the frangible element of the end portion of the encapsulation element is broken. Such a construction allows the sampling sorbent tube to be reusable and re-encapsulated by virtue of being preserved from damage during use. The construction also allows the sampling sorbent tube to be constructed a thicker wall of tubing well-suited for long shelf life and less prone to breakage during shipping, handling, and sampling. Further, the sampling sorbent tube may be extracted after breakage of the frangible encapsulation element with the certainty that the internal sorbent material of the sampling sorbent tube has not been prematurely exposed to pre-monitoring site air or gases during the prolonged period encompassing storage, shipment, handling, or transport.

Additional features and advantages of the present invention will become apparent to those skilled in the art from the following description and the accompanying figures illustrating preferred embodiments of the invention, the same being the present best mode for carrying out the invention.

BRIEF DESCRIPTION OF THE DRAWINGS

FIG. 3 is a cross sectional view of an encapsulated sorbent tube constructed in accordance with the teachings of the present invention.

FIG. 4 is a cross sectional view of an encapsulation element of the encapsulated sorbent tube of FIG. 3.

DESCRIPTION OF THE PREFERRED EMBODIMENT(S)

Figure 1:
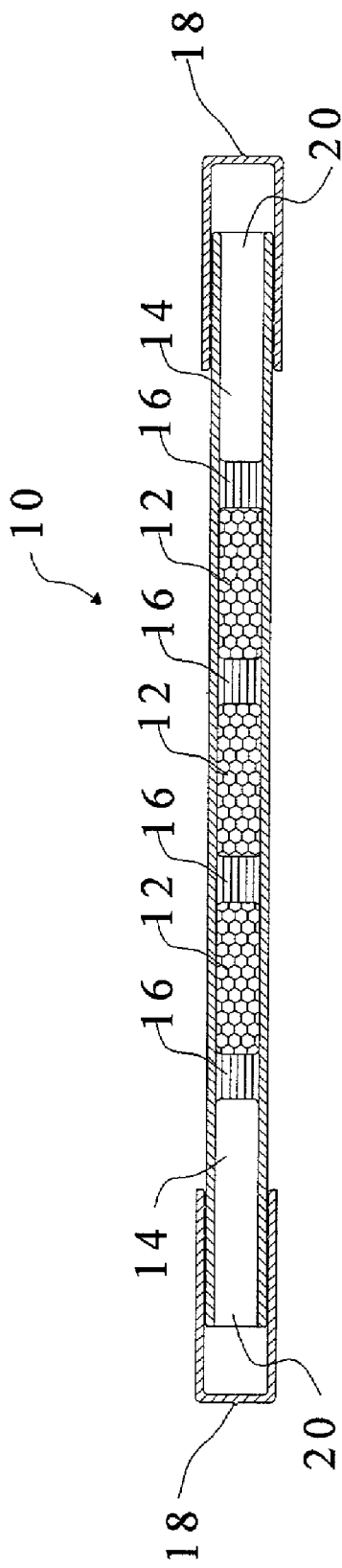
FIG. 1 is a cross sectional view of a typical "capped" prior art sampling sorbent tube containing sorbent material.
Figure 2:
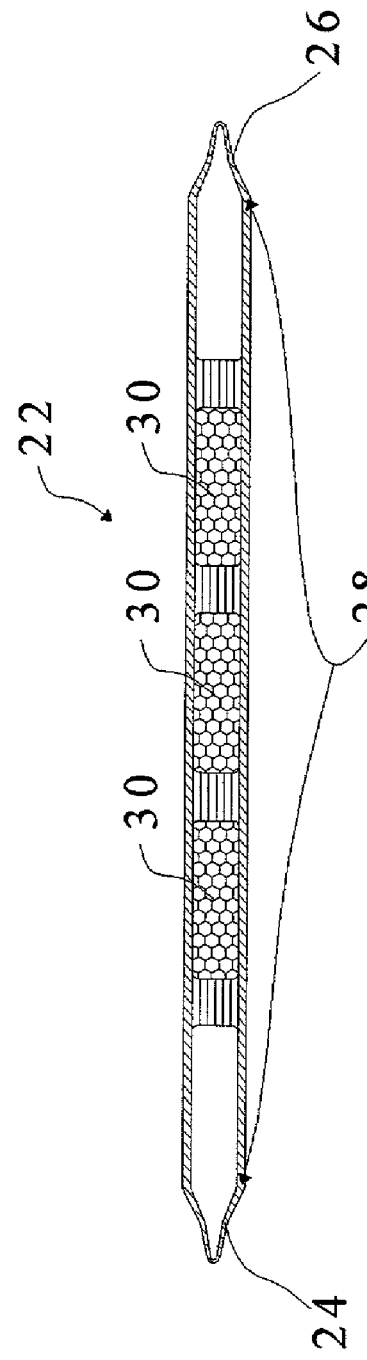
FIG. 2 is a cross sectional view of a typical "integral closed end" prior art sampling sorbent tube containing sorbent material.

Referring now to FIG. 1, there is illustrated an example of a typical prior art "capped" sampling sorbent tube 10 containing a sorbent material 12 in its interior core 14. The prior art "capped" sampling sorbent tube 10 includes one or more sorbent materials 12 capable of adsorbing volatilized chemicals from a gas stream or from the air. Sorbent materials 12 may be comprised of one or more adsorbents selected from a variety of different adsorbent materials known in the art, including charcoal, Tenax®, or carbon molecular sieve. For example, if a particular contaminant is being monitored, then use of a sorbent material that is tailored to adsorbing and trapping that particular contaminant offers advantages. However, if a user is monitoring ambient air for chemical contaminants having a range of activities or molecular weights, then the use of several among different absorbents as sorbent material 12 in the sampling sorbent tube 10 provides for obtaining complete and representative samples. The sorbent material 12 is ordinarily employed in particulate form and at an ordinary size range of 20/60 mesh. In any event, the movement of the singular or composite adsorbing sorbent material 12 with an interior core 14 of the sampling sorbent tube 10 is typically restrained in between a pair of shock absorbing porous plugs 16 which may be comprised of glass wool. Laterally displaced from the porous plugs 16 is a pair of over-caps 18 suited to cap over open ends 20 of the sampling sorbent tube. Upon removal of the over-caps 18 at a desired monitoring site, the arrangement of the porous plugs 16 and sorbent material 12 allows a reasonable free flowing of gas/air through the sampling sorbent tube during the sampling process while at the same time ensuring an extended contact between the gas/air and the sorbent material 12. At FIG. 2 there is illustrated an alternative prior art sampling sorbent tube 22 wherein the sampling sorbent tube itself is formed as an integral, closed construction having its lateral ends 24 and 26 sealed for a later breakage by a user at a monitoring site to then expose a central body portion 28 containing a desired sorbent material 30. The central body portion 28 of the alternative sampling sorbent tube 22 is illustrated to be identical to the prior art sampling sorbent tube 10 illustrated at FIG. 1 less the over-caps 18.

In contradistinction to the foregoing prior art sampling sorbent tubes, FIG. 3 illustrates an encapsulated sorbent tube 40 constructed in accordance with the teachings of the present invention. The encapsulated sorbent tube 40 includes a sampling sorbent tube 42 and an encapsulation element 44 independent of the sampling sorbent tube that has a body portion 46 and at least one end portion 48. The sampling sorbent tube 42 has open ends 50 and 52 and a sorbent material 54 contained in an interior core 56 of the sample sorbent tube 42 between a pair of shock absorbing porous plugs 58. The body portion 46 of the encapsulation element 44 has an inner diameter greater than the outer diameter of the sampling sorbent tube 42 sufficient to accommodate the sample sorbent tube 42 therein. The encapsulation element 44 has a longitudinal length (L) in excess of the sampling sorbent tube 42, the excess length (Lx) of which forms and defines the end portion 48. The end portion 48 is independent of and laterally separated from the sampling sorbent tube 42 contained within the interior of the body portion 46 of the encapsulation element 44. The end portion 48 includes a proximal frangible element 60 (proximal to the sampling sorbent tube 42) designed to enable a user to break away the end portion 48 from the encapsulation element 44 in such a way that the structural integrity of the sampling sorbent tube 42 is not compromised thereby through chipping, breakage, or the formation of stress lines or cracks. The proximal frangible element 60 may comprise a circumferential score 62 around the annular periphery 64 of the end portion 48 which weakens the end portion sufficiently at a defined point so that a user may bend and cleanly break the encapsulation element 44 at the circumferential score 62 without producing shards or fragments which may pose a hazard to the user. The circumferential score 62 may be achieved by circumferential scoring, diamond grove scratching, a thin wall construction, wall stretching during heating, or other known art means. The end portion 48 of the encapsulation element 44 also includes a distal closure seal 66 (distal to the sampling sorbent tube 42) functioning as a seal to a sampling sorbent tube 42 inserted within body portion 46 of the encapsulation element 44 to safeguard the same from pre-monitoring site air/gas exposure. After the encapsulated sorbent tube 40 arrives at a selected monitoring site, a breakage of the proximal frangible element 60 of the end portion 48 allows the sampling sorbent tube 42 to be removed from the body portion 46 of the encapsulation element 44 for gathering of the air or gas at a monitoring site of breakage. After sample collection, the sampling sorbent tube 42 may be capped and stored in a sealed test tube or other suitable device for transport back to the site of laboratory analysis. Thus, the encapsulation element 44 of the present invention maintains a continuous protective envelope over the sampling sorbent tube 42 until breakage of its frangible element at the time of monitoring site usage.

FIG. 4 illustrates the encapsulation element 44 without the sampling sorbent tube 42 contained therein. The body portion 46 of the encapsulation element 44 may be comprised of a glass envelope with a wall thickness sufficient to safeguard the sampling sorbent tube 42 to be contained therein. The end portion 48 of the encapsulation element 44 need not maintain a wall thickness greater than the body portion 46 since it is laterally displaced therefrom by the excess length (Lx) of the encapsulation element.

The encapsulation element 44 of the encapsulated sorbent tube device 40 is constructed from a single section of open-ended tubing made from glass, Pyrex®, or other, similar material. Before insertion of the sampling sorbent tube 42, one end of the singular section of tube forming encapsulation element 44 is heated until it is molten and a forms a distal closure seal 66. If desired, after the distal closure seal 66 of the tubing has cooled, a shock absorbing porous plug 68 of glass wool or some other cushioning device can be inserted through the remaining open end of the tubing section forming the encapsulation element 44 and pushed to a selected area within end portion 48. Then a sampling sorbent tube 42 packed with sorbent material 54 in its interior core 56 is then completely inserted through the remaining open end of the tubing section forming the encapsulation element 44 until it rests against the distal closure seal 66 or against the porous plug 68 previously inserted therein. If desired, a second porous plug 70 of glass wool or some other cushioning device can be likewise inserted through the remaining open end of the tubing section and pushed to rest against an end of the sampling sorbent tube 42 to further cushion it or to aid in keeping it in place during the remaining encapsulation procedure.

After the sampling sorbent tube 42 is in place in the encapsulation device, the device may, if desired, be evacuated or filled with a gas other than air before sealing of the remaining open end of the tubing section. After any such fill gas substitution has been accomplished, the tubing section forming the encapsulation element 44 is heated at a point above the sampling sorbent tube 42 being encapsulated to the liquidous temperature of the encapsulation element 44. The portion of the encapsulation element 44 thus heated is then drawn and heated to form another distal closure seal 72 at the previously remaining open end of the tubing section such that the material from which the encapsulation element 44 is made forms a continuous layer over the sampling sorbent tube 42 resulting in a sealed encapsulated sorbent tube 40 that is impervious to air exchange between the gas inside the encapsulation element 44 device and the air surrounding it.

After cooling, an end portion 48 of the encapsulation element 44 is circumferentially scored by circumferential scoring, diamond grove scratching, a thin wall construction, or wall stretching during heating to provide the proximal frangible element 60 of the end portion 48 comprised of circumferential score 62 so that when the end portion 48 is bent, a clean, complete fracture of the proximal frangible element 60 occurs at the point of circumferential score 62. The circumferential score 62 must not be deep enough to compromise the airtight nature of the encapsulation, however, it must be deep enough such that, when the encapsulation device is broken open, the break circumscribes the end portion perpendicular to the central axis of the encapsulation element 44 and reduces the probability that shards or fragments of the end portion are produced.

From the foregoing description, it will be apparent that the encapsulated sorbent tube of the present invention has a number of advantages, some of which have been described above and others of which are inherent in the invention. Also it will be understood that modifications can be made to the encapsulated sorbent tube described above or the sorbent contained therein without departing from the teachings of the present invention. Accordingly, the scope of the invention is only to be limited as necessitated by the accompanying claims.

I claim:

1. An encapsulated sorbent tube for sampling of air and gases comprising a removable sampling sorbent tube containing a solid adsorbent material disposed therein for collection adsorbing of volatilized chemicals from a gas stream or air, said sampling sorbent tube remaining in an unbroken condition prior to and during such collection and a contiguous encapsulation tube separate from and independent of said sorbent sampling tube having a body portion and an end portion to encapsulate and protect said sampling sorbent tube in said unbroken condition prior to its use for said collection, said body portion of said encapsulation tube having an inner diameter greater than the outer diameter of said sampling sorbent tube sufficient to encompass and accommodate said sampling sorbent tube therein, said encapsulation tube having a longitudinal length in excess of and extending from said sampling sorbent tube, such excess and extending length in part forming a first condition of said end portion of said encapsulation tube wherein said end portion is intact, said end portion of said encapsulation tube having a proximal score and a distal closure seal, said proximal score being located circumferentially upon said excess and extending length at a point of said end portion not in immediate adjacent proximity with said sampling sorbent tube and prior to said distal closure seal and said proximal score having a depth adapted for a circumferential breakage of said end portion of said encapsulation tube substantially perpendicular to the central longitudinal axis of said encapsulation tube at a point extending beyond and not in immediate adjacent proximity with said sampling sorbent tube and prior to said distal closure seal that defines a second condition of said end portion wherein said end portion is fractured to permit removal of said sampling sorbent tube in said unbroken condition.

2. The encapsulated sorbent tube of claim 1 wherein said encapsulation tube forms a complete integral continuous envelope to contain said sampling sorbent tube therein.

3. The encapsulated sorbent tube of claim 1 wherein said proximal score of said end portion comprises a circumferential score, a thinned wall portion, a stretched wall portion, or a groove of said end portion.

4. The encapsulated sorbent tube of claim 1 wherein said encapsulation tube is a glass envelope.

5. The encapsulated sorbent tube of claim 1 wherein said solid adsorbent material comprises a plurality of different adsorbents.

6. The encapsulated sorbent tube of claim 1 wherein said solid adsorbent material is in particulate form.

7. The encapsulated sorbent tube of claim 6 wherein said solid adsorbent material is in particulate form at a size range of 20/60 mesh.

* * * * *